United States Patent [19]

Conrad et al.

[11] 4,379,929
[45] Apr. 12, 1983

[54] 4(1H)-OXOCINNOLINE-3-CARBOXYLIC ACID DERIVATIVES

[75] Inventors: Robert A. Conrad, Indianapolis; William A. White, Fountaintown, both of Ind.

[73] Assignee: Eli Lilly and Company, Indianapolis, Ind.

[21] Appl. No.: 245,564

[22] Filed: Mar. 19, 1981

[51] Int. Cl.³ .............. C07D 237/28; C07D 491/04; C07D 9/65; A61K 31/495
[52] U.S. Cl. ................................. 544/234; 544/235; 424/250; 424/200
[58] Field of Search ....................... 544/235, 234

[56] References Cited

U.S. PATENT DOCUMENTS

| | | | |
|---|---|---|---|
| 3,591,697 | 7/1971 | Kaminsky et al. | 424/258 |
| 3,669,965 | 6/1972 | White | 260/250 A |
| 3,933,818 | 1/1976 | Jones | 544/235 |
| 4,027,023 | 5/1977 | Preston | 544/235 |
| 4,045,439 | 8/1977 | Preston et al. | 260/250 C |
| 4,060,530 | 11/1977 | Howarth et al. | 260/245.3 |
| 4,076,826 | 2/1977 | Christensen et al. | 260/245.3 |
| 4,085,103 | 4/1978 | Preston et al. | 260/250 C |
| 4,137,317 | 1/1979 | Paris et al. | 544/234 |
| 4,226,866 | 10/1980 | Christensen et al. | 546/183 |

FOREIGN PATENT DOCUMENTS 774033  4/1972  Belgium .

OTHER PUBLICATIONS

Burger's Medical Chemistry, 4th Edition, Part 2, pp. 68–69.
Cooper, et al., J. Amer. Chem. Soc. 70, 3966 (1948).
J. Heterocyclic Chem. 13:1085 (1976), R. Pauline Brundage and George Y. Lesher.
Bull. De La Soc. Chimique De France 8:3198 (1972).
Chem. Abstract 94:745–Abstract of J80,118,498.
Rodd's Chemistry of Carbon Compounds, Edited by S. Coffey, Chapter 23, p. 1, Chapter 26, pp. 231–234.
Condensed Pyridazines Including Cinnolines and Phthalazines, vol. 27, Chap. 1, pp. 1–12.
Quinolines, vol. 32, Edited by Gurnos Jones.

*Primary Examiner*—Mark L. Berch
*Attorney, Agent, or Firm*—Gerald V. Dahling; Arthur R. Whale

[57] ABSTRACT

Amide and ester derivatives of substituted-4(1H)-oxocinnoline-3-carboxylic acids have antibacterial activity and are useful for inhibiting the growth of disease causing bacteria.

12 Claims, No Drawings

4(1H)-OXOCINNOLINE-3-CARBOXYLIC ACID DERIVATIVES

BACKGROUND OF THE INVENTION

The present invention relates to novel amide and ester derivatives of substituted-4(1H)-oxocinnoline-3-carboxylic acids which are useful as antibacterials. While certain substituted-4(1H)-oxocinnoline-3-carboxylic acids are disclosed in U.S. Pat. No. 3,669,965 and German Pat. No. 2,005,104, and while certain esters are disclosed in U.S. Pat. No. 4,085,103, U.S. Pat. No. 4,045,439, Belgium Pat. No. 774,033, and the *Journal of Heterocyclic Chemistry* 13:1085 (1976), none of the present compounds are described, claimed, or taught in any of the above references. An additional reference, the *Bulletin De La Société Chimique De France* 8:3198 (1972), discloses esters and also a few cinnoline amide derivatives. However these compounds are also quite different from the compounds of the present invention and furthermore, the reference does not teach or suggest an antibacterial utility.

SUMMARY OF THE INVENTION

The invention is directed to compounds of the formula

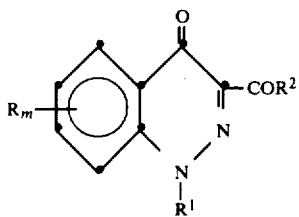

wherein
R represents methylenedioxy, halo, or nitro;
m = 1 or 2 subject to the limitation that when m = 2, each R is independently halo or nitro but both are not simultaneously nitro;
$R^1$ represents $C_1$-$C_3$ alkyl, n-butyl, or allyl;
$R^2$ represents $C_1$-$C_4$ alkoxy, hydroxy $C_2$-$C_4$ alkoxy, $NH_2$, $NHCH_2CH_2OH$, $NHCH_2CH_2SH$, $NHCH_2COOH$, $NHCH_2CH_2NH_2$,

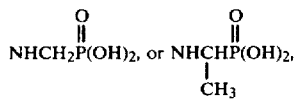

subject to the limitation that when any R represents halo or nitro, $R^2$ does not represent $C_1$-$C_4$ alkoxy or hydroxy $C_2$-$C_4$ alkoxy;
and wherein the position of R on the cinnoline ring is as follows:
1. when R represents methylenedioxy, R is at the 6,7-position of the cinnoline ring,
2. when R represents halo, R is at the 6-, 7-, or 6- and 7-positions of the cinnoline ring, or
3. when R represents nitro, R is at the 6- or 7-position of the cinnoline ring.

DETAILED DESCRIPTION OF THE INVENTION

For purposes of the present application, the compounds of this invention are named as derivatives of substituted-4(1H)-oxocinnoline-3-carboxylic acid with numbering as follows:

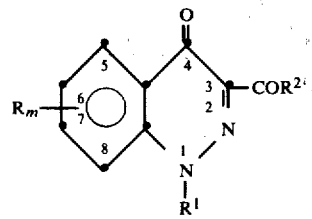

The ester and amides of the present invention are readily made by conventional procedures. For example, the esters are prepared by reacting the corresponding substituted-4(1H)-cinnoline-3-carboxylic acid with the corresponding alcohol previously saturated at 0° C. with dry hydrochloric acid. The primary amide compounds of the present invention are also prepared by known reactions involving a general procedure for the synthesis of amides as a class. Accordingly, the substituted-4(1H)-cinnoline-3-carboxylic acid starting material is heated with N,N'-carbonyldiimidazole at about 150° C. to 155° C. in water miscible aprotic solvents such as, for example, DMF, to give an imidazole which crystallizes upon cooling. The addition of an amine or amine salt, further heating at about 55° C. to 155° C., and subsequent precipitation by adding the mixture to ice water, gives the respective amide. Other methods such as the utilization of cinnoline acid chlorides, mixed anhydrides, or related reactions may also be used to make the desired amides and esters. Amides compounds can also be prepared by aminolysis of cinnoline esters according to conventional procedures.

The preparation of 1-alkyl or 1-allyl substituted-6,7-methylenedioxy-4(1H)-oxocinnoline-3-carboxylic acid as starting material for the above described synthesis of esters and amides, is known in the art and is substantially as taught in U.S. Pat. No. 3,669,965. Other halo or nitro substituted-4(1H)-oxocinnoline-3-carboxylic acid compounds which are also useful as starting materials are prepared according to the various synthetic routes which are presented and illustrated below. It is understood that the 1-non-substituted-4(1H)-oxocinnolines are tautomeric and also exist in the cinnoline-4-ol form as follows.

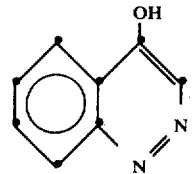

For convenience, they all will be referred to as 4(1H)-oxocinnolines in the reaction schemes and synthesis examples of the present application. The starting materials for the following synthetic routes are commercially available or can be synthesized readily by those skilled in the art.

I. Useful for R=halo and m=1 or 2 compounds, illustrated herein with R=Cl, m=2, and $R^1$=ethyl for simplicity.

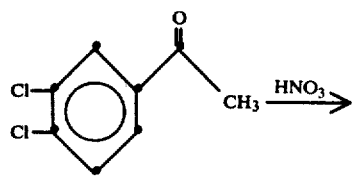
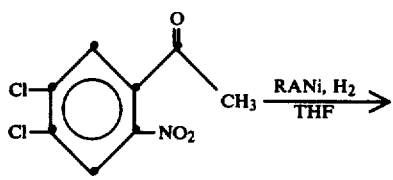
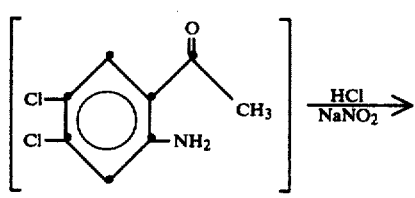
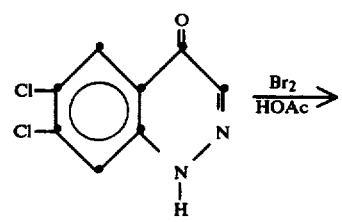
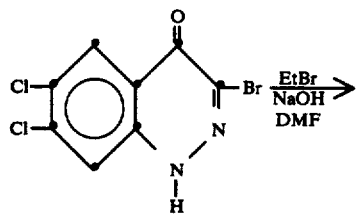
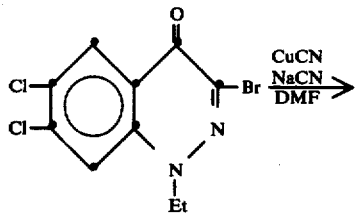
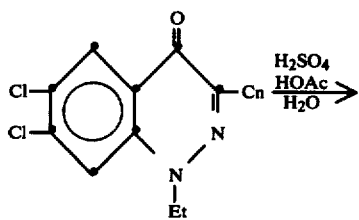
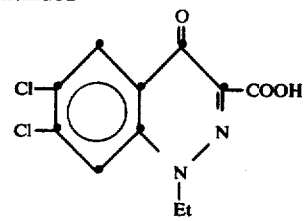
This synthetic route is illustrated by Examples 1 to 7.
II. Useful for R=nitro and m=1 compounds, illustrated herein with R at the 6-position and $R^1$=ethyl for simplicity.
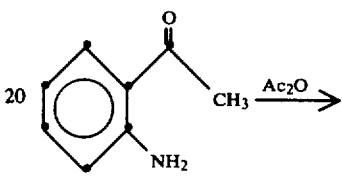
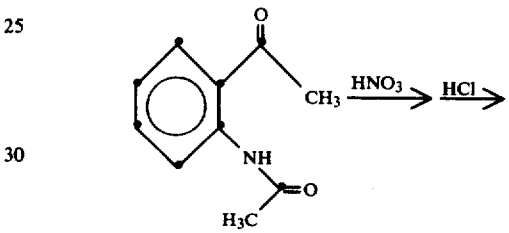
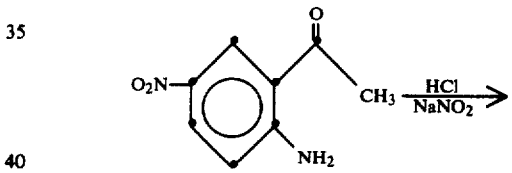
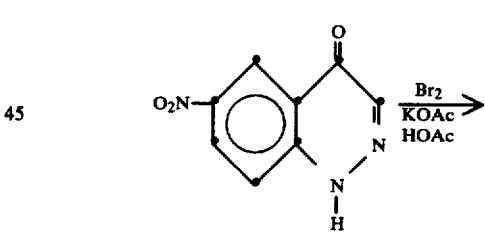
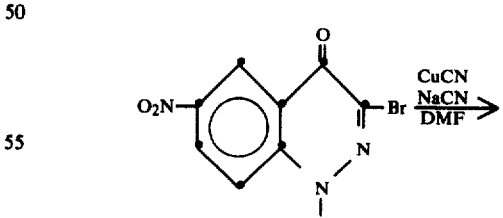
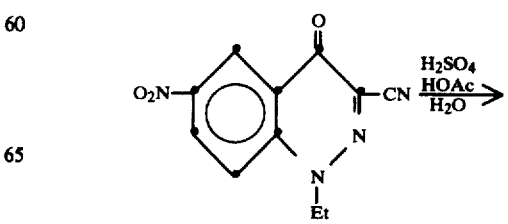

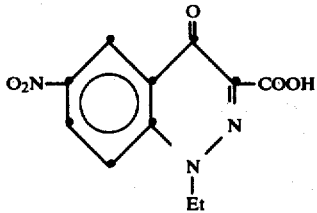

This synthetic route is illustrated by Examples 9 to 15.

III. Useful for m=2 compounds wherein one R=nitro and the other R=halo, illustrated herein with nitro at the 6-position, chloro at the 7-position, and $R^1$=ethyl for simplicity.

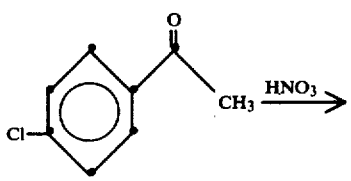

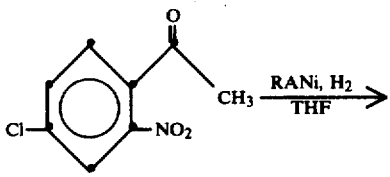

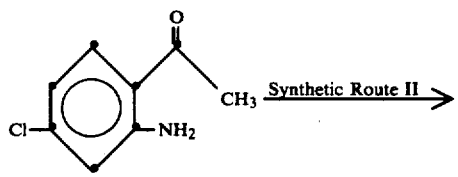

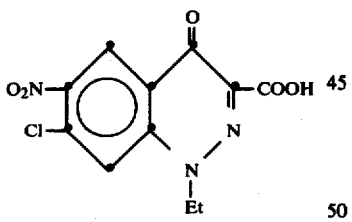

This synthetic route is illustrated by Examples 17 to 19.

The following examples illustrate the compounds of the present invention.

EXAMPLE 1

4,5-Dichloro-2-nitroacetophenone

About 200 grams of 3,4-dichloroacetophenone were reacted with about 1400 grams of 90% nitric acid at 33°–35° C. for about 1 hour. The reaction mixture was poured into about 4 l. of ice water and formed a precipitate which was filtered, dissolved in ethyl acetate, washed with water, and dried. Further precipitation from ethanol/petroleum ether yielded a pure product which was identified as the desired compound by NMR analysis, yield 70 grams, m.p. 98° C.

EXAMPLE 2

2-Amino-4,5-dichloroacetophenone

About 70 grams of 4,5-dichloro-3-nitroacetophenone in 625 ml. of tetrahydrofuran were subjected to hydrogenolysis overnight at ambient temperature by adding about 5 grams of Raney nickel and 50 psi hydrogen. The solution was filtered and evaporated in vacuo for use without further purification.

EXAMPLE 3

6,7-Dichloro-4(1H)-oxocinnoline

About 500 ml. of concentrated HCl were added to about 65 grams of 2-amino-4,5-dichloroacetophenone. After the reaction mixture was cooled to 0° C., about 21 grams of sodium nitrite in 150 ml. of water were added over 30 minutes. The resulting mixture was stirred at both ambient temperature and at 60° C. for 1 hour and 2 hours respectively. About 2 l. of ice water were added and a precipitate formed which was identified as the desired product by titration, mass spectroscopy, infrared spectroscopy, and elemental analysis; yield 35 grams.

EXAMPLE 4

3-Bromo-6,7-dichloro-4(1H)-oxocinnoline

About 36 grams of 6,7-dichloro-4(1H)-oxocinnoline were added to a solution comprising 16.5 grams of potassium acetate in 225 ml. of acetic acid. The resultant mixture was heated to reflux and a solution comprising 27 grams of bromine in 50 ml. of acetic acid was added slowly over ½ hour with stirring. After the addition of the bromine was completed, the reaction mixture was refluxed for 2 hours. The reaction mixture was allowed to cool to ambient temperature and was then poured into ½ l. of ice water. The resultant precipitate was recovered by filtration and washed with about 200 ml. of a 5 percent sodium bicarbonate solution. The precipitate was dried to yield the desired product which was confirmed by titration, mass spectroscopy, infrared spectroscopy, and elemental analysis; yield 48 grams.

EXAMPLE 5

3-Bromo-6,7-dichloro-1-ethyl-4(1H)-oxocinnoline

About 32 grams of 3-bromo-6,7-dichloro-4(1H)-oxocinnoline, 400 ml. of DMF, and 4.4 grams of sodium hydroxide were combined and heated until the sodium hydroxide dissolved. After cooling, about 12 grams of ethyl bromide were added slowly over 30 minutes. The resultant mixture was refluxed for 3 hours, cooled to ambient temperature, poured into 1 l. of water, and was made acidic with about 10 ml. of sulfuric acid. A precipitate formed which was determined by titration, mass spectroscopy, infrared spectroscopy, and elemental analysis to be the desired product; yield 28 grams.

EXAMPLE 6

6,7-Dichloro-1-ethyl-4(1H)-oxocinnoline-3-carbonitrile

About 16.1 grams of 3-bromo-6,7-dichloro-4(1H)-oxocinnoline and 5 grams of cuprous cyanide were refluxed in 50 ml. DMF under nitrogen for 3 hours. Next a solution comprising 7.5 grams of sodium cyanide in 50 ml. of hot water was added and the resultant reaction mixture was filtered hot. The precipitate thus collected was determined by mass spectroscopy, infrared spectroscopy, and elemental analysis to be the desired product; yield 7 grams.

EXAMPLE 7

6,7-Dichloro-1-ethyl-4(1H)-oxocinnoline-3-carboxylic acid

About 5 grams of 6,7-dichloro-1-ethyl-4(1H)-oxocinnoline-3-carbonitrile were refluxed for 4 hours with 30 ml. each of sulfuric acid, acetic acid, and water. Next the reaction mixture was poured into 600 ml. of water and filtered. The precipitate thus collected was taken up in 50 ml. of ammonium hydroxide and 200 ml. of water and was then treated with charcoal and heated. The resultant mixture was filtered and the filtrate added to a solution comprising 50 ml. of concentrated sulfuric acid and 400 ml. of water. This final mixture was filtered to yield a solid which was determined by titration, mass spectroscopy, infrared spectroscopy, and elemental analysis to be the desired product; yield 3.5 grams.

EXAMPLE 8

6,7-Dichloro-1-ethyl-4(1H)-oxocinnoline-3-carboxamide

About 5.24 grams of 6,7-dichloro-1-ethyl-4(1H)-oxocinnoline-3-carboxylic acid, 50 ml. of DMF, and about 3.64 grams of N,N'-carbonyldiimidazole are refluxed 1 hour. After cooling, about 4.62 grams of ammonium carbonate are added and the resultant mixture is stirred about 18 hours at ambient temperature. Next the reaction mixture is poured into ice water and a precipitate forms which is filtered and dried. The precipitate thus collected constitutes the desired product.

EXAMPLE 9

2-Acetylaminoacetophenone

About 200 grams of 2-aminoacetophenone were added to about 350 ml. of acetic anhydride at 0° C. After warming to ambient temperature, the reaction mixture was stirred 4 hours and, upon addition of ice water, a precipitate formed which was filtered and washed with water. The precipitate was suspended in ether and washed separately with 1 l. each of 1 N sodium hydroxide, water, 1 N hydrochloric acid, and again with 1 N sodium hydroxide. The ether suspension was dried with sodium sulfate, filtered, and concentrated. Ligroin was added and the desired product was collected by filtration. The identity of the final product was confirmed by NMR analysis; yield 215 grams, m.p. 69° C.

EXAMPLE 10

2-Amino-5-nitroacetophenone

About 50 grams of 2-acetylaminoacetophenone were added slowly over 1 hour at approximately 0° C. to about 250 ml. of 90% nitric acid and about 50 ml. of sulfuric acid. After the reaction mixture was stirred 1 hour, ice was added and a precipitate formed which was filtered, washed with water, and dried. Next 230 ml. each of ethanol, hydrochloric acid, and water were added and the resultant mixture was refluxed allowing the ethanol to be boiled off. Upon cooling, a crude product formed which was collected and reprecipitated from ethyl acetate/petroleum ether. The identity of the final product was confirmed by NMR and elemental analysis, yield 29 grams, m.p. 145°–146° C.

EXAMPLE 11

6-Nitro-4(1H)-oxocinnoline

About 18 grams of 2-amino-5-nitroacetophenone were added to 200 ml. of concentrated hydrochloric acid at approximately 0° C. Next about 8 grams of sodium nitrite in 30 ml. of water were added slowly and the resultant mixture was stirred 30 minutes, heated on a steam bath 1 hour, and then refluxed 1 hour. Upon cooling, a precipitate formed which was filtered, washed with water, and dried. The identity of the final product was confirmed by mass spectroscopy, infrared spectroscopy, and elemental analysis; m.p. >250° C.

EXAMPLE 12

3-Bromo-6-nitro-4(1H)-oxocinnoline

About 9.55 grams of 6-nitro-4(1H)-oxocinnoline were refluxed in a solution comprising about 5 grams of potassium acetate in 65 ml. of acetic acid. Next about 8 grams of bromine in 20 ml. of acetic acid were added and the resultant mixture was refluxed ½ hour, cooled, and added to 150 ml. of ice water. A precipitate formed which was filtered, washed with 5% aqueous sodium bicarbonate, and dried. The identity of the final product was confirmed by NMR and elemental analysis; yield 10 grams.

EXAMPLE 13

3-Bromo-1-ethyl-6-nitro-4(1H)-oxocinnoline

About 8.8 grams of sodium hydroxide were added to about 60 grams of 3-bromo-6-nitro-4(1H)-oxocinnoline in 600 ml. DMF and stirred 1 hour. Next about 24 grams of ethyl bromide were added and the resultant mixture was stirred at ambient temperature 1 hour and refluxed 2 hours. Upon cooling, 1 l. of ice water was added and also sufficient hydrochloric acid to make the reaction acidic. Filtering yielded a tar-like first crop which was disgarded. The desired product, confirmed by NMR and elemental analysis, was obtained in the second crop.

EXAMPLE 14

1-Ethyl-6-nitro-4(1H)-oxocinnoline-3-carbonitrile

About 3.6 grams of cuprous cyanide were added to about 6 grams of 3-bromo-1-ethyl-6-nitro-4(1H)-oxocinnoline in 100 ml. of DMF and refluxed 1 hour. Upon cooling, about 3 grams of sodium cyanide in 200 ml. of water were added and the resultant mixture was filtered. A portion of the precipitate was heated in ethyl acetate with charcoal, silica, and sodium sulfate. Next the mixture was filtered and concentrated to yield the desired product, the identity of which was confirmed by mass spectroscopy, infrared spectroscopy, and elemental analysis.

EXAMPLE 15

1-Ethyl-6-nitro-4(1H)-oxocinnoline-3-carboxylic acid

About 477 grams of 1-ethyl-6-nitro-4(1H)-oxocinnoline-3-carbonitrile were refluxed 3 hours in a mixture of 1.2 l. each of sulfuric acid and acetic acid, and 1 l. of water. Next about 15 l. of ice were added and a precipitate formed which was collected and dissolved in 1 N sodium hydroxide. The latter mixture was filtered and the filtrate acidified. A precipitate formed which was collected by filtration and shown by infrared spectroscopy and titration analysis to be the desired product; yield 35 grams.

Calculated: C, 50.20; H, 3.45; N, 15.92.* Found: C, 46.43; H, 3.57; N, 15.13.*
*With oxygen comprising the remainder.

EXAMPLE 16

1-Ethyl-6-nitro-4(1H)-oxocinnoline-3-carboxamide

About 5.2 grams of 1-ethyl-6-nitro-4(1H)-oxocinnoline-3-carboxylic acid, 50 ml. of DMF, and about 3.6 grams of N,N'-carbonyldiimidazole were refluxed 10 minutes. After cooling, 10 grams of ammonium carbonate were added and the resultant mixture was stirred about 1 hour at ambient temperature. Next the reaction mixture was poured into ice water and a precipitate formed which was filtered an dried. Infrared spectroscopy and titration analysis confirmed that the precipitate was the desired product.

Calculated: C, 50.38; H, 3.84; N, 21.37.* Found: C, 50.20; H, 4.04; N, 21.12.*
*With oxygen comprising the remainder.

EXAMPLE 17

4-Chloro-2-nitroacetophenone

This compound is prepared according to the teaching of Example 1 using 4-chloroacetophenone as starting material.

EXAMPLE 18

2-Amino-4-chloroacetophenone

This compound is prepared from 4-chloro-2-nitroacetophenone according to the teaching of Example 2.

EXAMPLE 19

7-Chloro-1-ethyl-6-nitro-4(1H)-oxocinnoline-3-carboxylic acid

This compound is prepared from 2-amino-4-chloroacetophenone according to the teaching of synthesis route II, Examples 9 to 15.

EXAMPLE 20

7-Chloro-1-ethyl-N-(2-hydroxyethyl)-6-nitro-4(1H)-oxocinnoline-3-carboxamide

About 5.2 grams of 7-chloro-1-ethyl-6-nitro-4(1H)-oxocinnoline-3-carboxylic acid, 50 ml. of DMF, and about 3.6 grams of N,N'-carbonyldiimidazole are refluxed 1 hour. After cooling, about 4.6 grams of 2-hydroxyethylamine are added and the resultant mixture is stirred about 18 hours at ambient temperature. Next the reaction mixture is poured into ice water and a precipitate forms which is filtered and dried. The precipitate thus collected constitutes the desired product.

EXAMPLE 21

1-Ethyl-N-(2-mercaptoethyl)-6,7-methylene-dioxy-4(1H)-oxocinnoline-3-carboxamide About 5.2 grams of 1-ethyl-6,7-methylene-dioxy-4(1H)-oxocinnoline-3-carboxylic acid (prepared according to the teaching of U.S. Pat. No. 3,669,965), 50 ml. of DMF, and about 3.6 grams of N,N'-carbonyldiimidazole were refluxed for 1 hour. After cooling, about 2.3 grams of 2-mercaptoethylamine hydrochloride were added and the resultant mixture was stirred about 1 hour at ambient temperature. Next the reaction mixture was poured into acidified ice water and a precipitate formed which was filtered and dried. Infrared spectroscopy and titration analysis confirmed that the precipitate constituted the desired product.

Calculated: C, 52.33; H, 4.71; N, 13.08; S, 9.98.* Found: C, 53.69; H, 4.32; N, 12.40; S, 7.80.*
*With oxygen comprising the remainder.

It will be understood by those skilled in the art that one can readily employ the procedure disclosed in Examples 8, 16, 20, and 21 for the preparation of other amides of the present invention by substituting other amine sources and amines such as, for example, glycine, aminomethylphosphonic acid, aminoethylphosphonic acid, or diaminoethane for the ammonium carbonate, 2-hydroxyethylamine, and 2-mercaptoethylamine hydrochloride exemplified respectively therein.

EXAMPLE 22

1-Ethyl-6,7-methylenedioxy-4(1H)-oxocinnoline-3-carboxylic acid, methyl ester

About 10 grams of 1-ethyl-6,7-methylenedioxy-4(1H)-oxocinnoline-3-carboxylic acid (prepared according to the teaching of U.S. Pat. No. 3,669,965) were refluxed 3 hours in 500 ml. of methanol which was previously saturated at 0° C. with dry HCl. The resultant mixture was cooled and stirred for about 18 hours at ambient temperature. Next the solvent was removed in vacuo and water and sodium bicarbonate were added until the reaction mixture became basic. A crude solid product was obtained by extraction with chloroform, drying other sodium sulfate, filtering, and evaporating the solvent. The crude solid was dissolved in chloroform, precipitated with petroleum ether, filtered, and dried. Mass spectroscopy, infrared spectroscopy, and elemental analysis confirmed that the final product was the desired compound.

Calculated: C, 56.52; H, 4.38; N, 10.14.* Found: C, 56.37; H, 4.21; N, 10.18.*
*With oxygen comprising the remainder.

It will be understood by those skilled in the art that one can readily employ the procedure disclosed in Example 22 for the preparation of other esters of the present invention by substituting other alcohols for the methanol which, for illustration, is exemplified therein.

Other representative examples synthesized in accordance with the foregoing teaching include the following:

| Example No. | Compound |
|---|---|
| 23 | 1-ethyl-6,7-methylenedioxy-4(1H)-oxocinnoline-3-carboxamide, m.p. >250° C. |
| 24 | 1-ethyl-6,7-methylenedioxy-4(1H)-oxocinnoline-3-carboxylic acid, 2-hydroxyethyl ester |
| 25 | 1-ethyl-N—(2-hydroxyethyl)-6,7-methylene-dioxy-4(1H)-oxocinnoline-3-carboxamide |
| 26 | N—(carboxymethyl)-1-ethyl-6,7-methylene-dioxy-4(1H)-oxocinnoline-3-carboxyamide |
| 27 | N—(2-aminoethyl)-1-ethyl-6,7-methylene-dioxy-4(1H)-oxocinnoline-3-carboxyamide |

Additional representative compounds that are within the scope of the present invention and that can be synthesized in accordance with the foregoing teaching include the following:

1-methyl-6,7-methylenedioxy-4(1H)-oxocinnoline-3-carboxamide 1-isopropyl-6,7-methylenedioxy-4(1H)-oxocinnoline-3-carboxamide 1-methyl-6,7-methylenedioxy-4(1H)-oxocinnoline-3-carboxylic acid, methyl ester
1-n-propyl-6,7-methylenedioxy-4(1H)-oxocinnoline-3-carboxylic acid, methyl ester
1-allyl-6,7-methylenedioxy-4(1H)-oxocinnoline-3-carboxylic acid, methyl ester
1-methyl-6,7-methylenedioxy-4(1H)-oxocinnoline-3-carboxylic acid, 2-hydroxyethyl ester
1-n-propyl-6,7-methylenedioxy-4(1H)-oxocinnoline-3-carboxylic acid, 2-hydroxyethyl ester
1-isopropyl-6,7-methylenedioxy-4(1H)-oxocinnoline-3-carboxylic acid, 2-hydroxyethyl ester
1-n-butyl-6,7-methylenedioxy-4(1H)-oxocinnoline-3-carboxylic acid, 2-hydroxyethyl ester
1-allyl-6,7-methylenedioxy-4(1H)-oxocinnoline-3-carboxylic acid, 2-hydroxyethyl ester
N-(2-hydroxyethyl)-1-methyl-6,7-methylenedioxy-4(1H)-oxocinnoline-3-carboxamide
N-(2-hydroxyethyl)-1-n-propyl-6,7-methylenedioxy-4(1H)-oxocinnoline-3-carboxamide
1-n-butyl-N-(2-hydroxyethyl)-6,7-methylenedioxy-4(1H)-oxocinnoline-3-carboxamide
1-allyl-N-(2-hydroxyethyl)-6,7-methylenedioxy-4(1H)-oxocinnoline-3-carboxamide
N-carboxymethyl-1-methyl-6,7-methylenedioxy-4(1H)-oxocinnoline-3-carboxamide
1-ethyl-6,7-methylenedioxy-N-methylphosphonic acid-4(1H)-oxocinnoline-3-carboxamide
1-ethyl-N-ethylphosphonic acid-6,7-methylenedioxy-4(1H)-oxocinnoline-3-carboxamide
N-carboxymethyl-1-isopropyl-6,7-methylenedioxy-4(1H)-oxocinnoline-3-carboxamide
1-n-butyl-N-carboxymethyl-6,7-methylenedioxy-4(1H)-oxocinnoline-3-carboxamide
1-allyl-N-carboxymethyl-6,7-methylenedioxy-4(1H)-oxocinnoline-3-carboxamide
N-(2-mercaptoethyl)-1-methyl-6,7-methylenedioxy-4(1H)-oxocinnoline-3-carboxamide
N-(2-mercaptoethyl)-1-n-propyl-6,7-methylenedioxy-4(1H)-oxocinnoline-3-carboxamide
1-isopropyl-N-(2-mercaptoethyl)-6,7-methylenedioxy-4(1H)-oxocinnoline-3-carboxamide
1-n-butyl-N-(2-mercaptoethyl)-6,7-methylenedioxy-4(1H)-oxocinnoline-3-carboxamide
1-allyl-N-(2-mercaptoethyl)-6,7-methylenedioxy-4(1H)-oxocinnoline-3-carboxamide
1-methyl-6-nitro-4(1H)-oxocinnoline-3-carboxamide
1-ethyl-7-nitro-4(1H)-oxocinnoline-3-carboxamide
1-methyl-7-nitro-4(1H)-oxocinnoline-3-carboxamide
1-ethyl-N-(2-hydroxyethyl)-6-nitro-4(1H)-oxocinnoline-3-carboxamide
N-(carboxymethyl)-1-ethyl-6-nitro-4(1H-oxocinnoline-3-carboxamide
1-allyl-N-(carboxymethyl)-6-nitro-4(1H)-oxocinnoline-3-carboxamide
N-(carboxymethyl)-1-isopropyl-6-nitro-4(1H)-oxocinnoline-3-carboxamide
1-ethyl-N-(2-mercaptoethyl)-7-nitro-4(1H)-oxocinnoline-3-carboxamide
6-chloro-1-ethyl-N-(2-hydroxyethyl)-7-nitro-4(1H)-oxocinnoline-3-carboxamide
7-chloro-N-(2-hydroxyethyl)-1-methyl-6-nitro-4(1H)-oxocinnoline-3-carboxamide
6,7-dichloro-1-ethyl-N-(2-hydroxyethyl)-4(1H)-oxocinnoline-3-carboxamide
6,7-dibromo-1-methyl-N-(2-hydroxyethyl)-4(1H)-oxocinnoline-3-carboxamide
1-n-butyl-6,7-difluoro-N-(2-hydroxyethyl)-4(1H)-oxocinnoline-3-carboxamide
6-chloro-1-ethyl-N-(2-hydroxyethyl)-4(1H)-oxocinnoline-3-carboxamide
7-fluoro-1-isopropyl-N-(2-hydroxyethyl)-4(1H)-oxocinnoline-3-carboxamide The novel compounds of the present invention show good antibacterial activity and are effective against a wide array of pathogenic microorganisms. More particularly, the compounds are especially effective against Mycoplasma, Pasteurella, and the enteric bacilli such as, for example, Enterobacter, *Eschericia coli*, Klebsiella, Proteus, and Salmonella, and also against various cocci including, for example, Staphylococcus and Streptococcus. Consequently the compounds of the present invention are important for inhibiting the growth of disease causing bacteria which cause health related problems for people, cattle, swine, fowl, and warm blooded animals generally.

Representative novel compounds of this invention were tested in vitro to demonstrate their effectiveness as antibacterial agents. The tests were performed by the agar-dilution and disk agar-diffusion methods and were carried out over a 24 hour period.

In the agar-dilution test, the test compounds were prepared at concentrations of 100 μg./ml. and 10 μg./ml. in liquid (melted) agar medium and were poured into separate petri dishes and allowed to solidify at ambient temperature to form agar plates. Suspensions containing about $10^4$ test organisms/5 μl. were applied in 5 μl. volumes as discreet spots on the surfaces of the agar plates. After the plates were incubated for 24 hours at 30° C., the absence of visible growth at the spot of inoculation was interpreted as indicating activity of the test compound. The viability of the inocula was confirmed by observing several control plates which contained the inocula but not the test compound.

Results of the agar-dilution test for representative compounds of the present invention are shown in Table 1. The antibacterial activity is scored as follows:

<10 μg./ml.—no growth on either the 10 μg./ml. or the 100 μg./ml. plate.

100 μg./ml.—growth on the 10 μg./ml. plate but not on the 100 μg./ml. plate.

N/A—growth on both plates.

Test cultures of *Pseudomonas solanacearum* required an additional incubation period for 48 hours at 24° C. to establish growth on the control plate. End points for this organism were therefore delayed until after the second incubation period.

TABLE 1

| | IN VITRO ANTIBIOTIC ACTIVITY | | | | | | |
|---|---|---|---|---|---|---|---|
| TEST ORGANISM BACTERIA | Inhibitory Concentration of Test Compound In mg./ml. | | | | | | |
| | Ex. 16 | Ex. 21 | Ex. 22 | Ex. 23 | Ex. 24 | Ex. 25 | Ex. 26 |
| *Staphylococcus aureus* 3055 | 100 | 100 | 100 | N/A | 100 | 100 | 100 |
| *Staphylococcus aureus* 3074 | 100 | 100 | N/A | N/A | 100 | 100 | 100 |
| *Streptococcus faecalis* X66 | N/A | N/A | N/A | N/A | N/A | 100 | 100 |
| *Proteus morganii* PR15 | N/A | <10 | 100 | 100 | 100 | 100 | 100 |

TABLE 1-continued
IN VITRO ANTIBIOTIC ACTIVITY

| TEST ORGANISM BACTERIA | Inhibitory Concentration of Test Compound In mg./ml. | | | | | | |
|---|---|---|---|---|---|---|---|
| | Ex. 16 | Ex. 21 | Ex. 22 | Ex. 23 | Ex. 24 | Ex. 25 | Ex. 26 |
| *Salmonella typhosa* SA12 | N/A | <10 | 100 | 100 | <10 | <10 | <10 |
| *Klebsiella pneumoniae* KL14 | N/A | <10 | N/A | N/A | N/A | N/A | <10 |
| *Enterbacter aerogenes* EB17 | N/A | <10 | 100 | 100 | 100 | <10 | <10 |
| *Serratia marcescens* SE3 | N/A | 100 | N/A | N/A | 100 | 100 | 100 |
| *Escherichia coli* EC15 | N/A | 100 | 100 | 100 | 100 | <10 | 100 |
| *Citrobacter freundii* CF17 | N/A | <10 | 100 | 100 | 100 | <10 | <10 |
| *Pseudomonas aeruginosa* X239 | N/A | N/A | N/A | N/A | N/A | N/A | N/A |
| *Bordetella bronchiseptica* 16 | N/A | 100 | N/A | N/A | N/A | N/A | 100 |
| *Salmonella typhimurium* | N/A | <10 | 100 | 100 | 100 | <10 | <10 |
| *Pseudomonas solanacearum* X185 | N/A | 100 | 100 | 100 | 100 | 100 | 100 |
| *Erwinia amylovora* | N/A | N/A | N/A | N/A | N/A | N/A | N/A |

The novel compounds of this invention are effective in combating bacterial infections in warm blooded animals when administered in total daily amounts of from about 25 mg. to about 500 mg./kg. of body weight.

While all the compounds of the present invention show considerable efficacy as antibacterials and consequently inhibit the growth of pathogenic bacteria, certain compounds are more effective than others. Accordingly, preferred compounds of this invention are amides wherein R represents methylenedioxy and $R^1$ represents $C_1$-$C_3$ alkyl, n-butyl, or allyl. One of the most useful and preferred compounds of this group is 1-ethyl-N-(2-mercaptoethyl)-6,7-methylenedioxy-4(1H)-oxocinnoline-3-carboxamide. Additional compounds which are also preferred include 1-ethyl-N-(2-hydroxyethyl)-6,7-methylenedioxy-4(1H)-oxocinnoline-3-carboxamide and N-(carboxymethyl)-1-ethyl-6,7-methylenedioxy-4(1H)-oxocinnoline-3-carboxamide.

In an important embodiment of the present invention, 1-ethyl-N-(2-mercaptoethyl)-6,7-methylenedioxy-4(1H)-oxocinnoline-3-carboxamide is administered orally in a suitable animal feed in which the compound is present in an amount of from about 25 to about 2500 grams per ton of total feed. The addition of the compounds of this invention to feed is preferably accomplished by preparing an appropriate feed premix and incorporating the premix into the complete ration. Alternatively, an intermediate concentrate or feed supplement containing the compound can be blended into the feed.

The preparation of a suitable feed premix can be effected by grinding the compounds of this invention to a powder and admixing with a suitable carrier such as alfalfa grits, solvent-extracted soybean feed, corn meal, exfoliated hydrobiotite, and like carriers. The premix so prepared is then admixed with whatever feed ration that is being fed to the animal at the time of administering the compounds of this invention. The feed premix can first be diluted with a feed supplement or feed concentrate to a desired concentration of the active compound, and the medicated supplement or concentrate can either be fed concurrently with the remainder of the ration or can be mixed into the final feed.

An alternate procedure for preparing the premix comprises the addition of a solution or slurry of the active compound to the premix carrier by spraying onto the carrier with suitable mixing. A solution can be prepared by slurrying the active compound in water and then titrating with a base such as sodium hydroxide solution to a pH of 6.5 to 8.5, or by dissolving the active compound in a suitable solvent such as N,N-dimethylacetamide or ethanol. A slurry of the compound can be prepared in an aqueous system or other appropriate vehicle such as an edible vegetable oil or an edible glycol.

The present compounds can be administered as a single dose or in divided doses either in parenteral or oral dosage form. When a parenteral dosage form is indicated, the active agent can be suspended in an aqueous or oil vehicle such as ethyl oleate or the compound may be dissolved in a solvent such as N,N-dimethylacetamide or dissolved in water by titrating an aqueous slurry with a base such as sodium hydroxide solution to a pH of 6.5 to 8.5, in a concentration of from about 25 to about 400 mg./ml and then a given dose can be conveniently injected into an animal.

The novel compounds of this invention can also be administered orally in one of the customary oral dosage forms; for example, filled capsules, liquids, suspensions, compressed tablets, and the like. Such oral dosage forms customarily contain the desired amount of active compound along with appropriate fillers, binders, solvents, vehicles, preservatives, and other excipients.

Illustratively, 1-ethyl-N-(2-hydroxyethyl)-6,7-methylenedioxy-4(1H)-oxocinnoline-3-carboxamide can be processed into tablets suitable for oral administration by the following procedure: 5.0 gm. of 1-ethyl-N-(2-hydroxyethyl)-6,7-methylenedioxy-4(1H)-oxocinnoline-3-carboxamide are mixed with 22.0 gm. of lactose, 2.9 gm. of starch, and 0.1 gm. of magnesium stearate, and the mixture is pressed into tablets of such size that each tablet contains 50 mg. of the active agent. It will be understood by those skilled in the formulation art, that the above illustrative procedure can be applied for formulating any of the other compounds of the present invention and furthermore, that the resulting tablets can contain varying amounts of the active agent depending upon a specific treatment need, tablet size, compound concentration, and convenience in processing.

I claim:
1. Compound of the formula

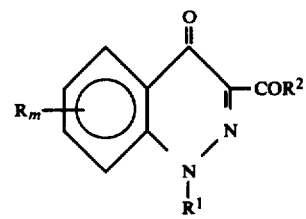

wherein
R represents methylenedioxy, or nitro;

m=1;

R¹ represents C₁–C₃ alkyl, n-butyl, or allyl;

R² represents hydroxy C₂–C₄ alkoxy, NHCH₂CH₂OH, NHCH₂CH₂SH, NHCH₂COOH, NHCH₂CH₂NH₂,

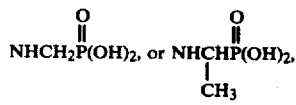

subject to the limitation that when R represents nitro, R² represents NHCH₂CH₂SH;

and wherein the position of R on the cinnoline ring is as follows:

1. when R represents methylenedioxy, R is at the 6,7-position of the cinnoline ring, or 2. when R represents nitro, R is at the 7-position of the cinnoline ring.

2. The compound of claim 1 wherein R² is hydroxy C₂–C₄ alkoxy.

3. The compound of claim 1 which is 1-ethyl-N-(2-mercaptoethyl)-7-nitro-4(1H)-oxocinnoline-3-carboxamide.

4. The compound of claim 2 which is 1-ethyl-6,7-methylenedioxy-4(1H)-oxocinnoline-3-carboxylic acid, 2-hydroxyethyl ester.

5. The compound of claim 1 wherein R is methylenedioxy and R² is NHCH₂CH₂OH, NHCH₂CH₂SH, NHCH₂COOH, NHCH₂CH₂NH₂,

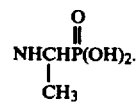

6. The compound of claim 5 which is 1-ethyl-N-(2-hydroxyethyl)-6,7-methylenedioxy-4(1H)-oxocinnoline-3-carboxamide.

7. The compound of claim 5 which is N-(carboxymethyl)-1-ethyl-6,7-methylenedioxy-4(1H)-oxocinnoline-3-carboxamide.

8. The compound of claim 5 which is 1-ethyl-N-(2-mercaptoethyl)-6,7-methylenedioxy-4(1H)-oxocinnoline-3-carboxamide.

9. The compound of claim 5 which is N-(2-aminoethyl)-1-ethyl-6,7-methylenedioxy-4(1H)-oxocinnoline-3-carboxamide.

10. The compound of claim 5 which is 1-ethyl-6,7-methylenedioxy-N-methylphosphonic acid-4(1H)-oxocinnoline-3-carboxamide.

11. The compound of claim 5 which is 1-ethyl-N-ethylphosphonic acid-6,7-methylenedioxy-4(1H)-oxocinnoline-3-carboxamide.

12. The compound of claim 5 which is selected from the group consisting of N-(2-hydroxyethyl)-1-methyl-6,7-methylenedioxy-4(1H)-oxocinnoline-3-carboxamide, N-(2-hydroxyethyl)-1-n-propyl-6,7-methylenedioxy-4(1H)-oxocinnoline-3-carboxamide, 1-n-butyl-N-(2-hydroxyethyl)-6,7-methylenedioxy-4(1H)-oxocinnoline-3-carboxamide, N-carboxymethyl-1-isopropyl-6,7-methylenedioxy-4(1H)-oxocinnoline-3-carboxamide, N-(2-mercaptoethyl)-1-methyl-6,7-methylenedioxy-4(1H)-oxocinnoline-3-carboxamide, N-(2-mercaptoethyl)-1-n-propyl-6,7-methylenedioxy-4(1H)-oxocinnoline-3-carboxamide, 1-isopropyl-N-(2-mercaptoethyl)-6,7-methylenedioxy-4(1H)-oxocinnoline-3-carboxamide, 1-n-butyl-N-(2-mercaptoethyl)-6,7-methylenedioxy-4(1H)-oxocinnoline-3-carboxamide, and 1-allyl-N-(2-mercaptoethyl)-6,7-methylenedioxy-4(1H)-oxocinnoline-3-carboxamide.

* * * * *